(12) United States Patent
La Rochelle et al.

(10) Patent No.: US 9,346,863 B2
(45) Date of Patent: May 24, 2016

(54) FISH PROTEIN HYDROLYSATE HAVING A BONE-STIMULATING AND MAINTAINING ACTIVITY, NUTRACEUTICAL AND PHARMACOLOGICAL COMPOSITIONS COMPRISING SUCH A HYDROLYSATE AND METHOD FOR OBTAINING SAME

(71) Applicant: COMPAGNIE DES PECHES SAINT MALO SANTE, Saint-Malo (FR)

(72) Inventors: Hubert Drieu La Rochelle, Saint-Malo (FR); Elisa Courois, Saint-Malo (FR)

(73) Assignee: Compagnie des Peches Saint Malo Sante, Saint-Malo (FR)

( * ) Notice: Subject to any disclaimer, the term of this patent is extended or adjusted under 35 U.S.C. 154(b) by 50 days.

(21) Appl. No.: 14/090,603

(22) Filed: Nov. 26, 2013

(65) Prior Publication Data
US 2014/0221293 A1    Aug. 7, 2014

Related U.S. Application Data

(63) Continuation of application No. 12/866,867, filed as application No. PCT/EP2009/051655 on Feb. 12, 2009, now abandoned.

(30) Foreign Application Priority Data

Feb. 12, 2008    (FR) ..................... 08 00753

(51) Int. Cl.
| | |
|---|---|
| A23L 1/305 | (2006.01) |
| C07K 14/46 | (2006.01) |
| A23J 3/34 | (2006.01) |
| A61K 35/60 | (2006.01) |
| A61K 38/01 | (2006.01) |
| C12P 21/06 | (2006.01) |

(52) U.S. Cl.
CPC ............... *C07K 14/461* (2013.01); *A23J 3/346* (2013.01); *A23L 1/3053* (2013.01); *A61K 35/60* (2013.01); *A61K 38/012* (2013.01); *C12P 21/06* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2005/0164950 | A1 | 7/2005 | Fogelman et al. |
| 2011/0039768 | A1 | 2/2011 | Drieu La Rochelle et al. |
| 2012/0238492 | A1 | 9/2012 | Courois et al. |

FOREIGN PATENT DOCUMENTS

| | | |
|---|---|---|
| EP | 1273239 | 1/2003 |
| FR | 2835703 | 8/2003 |
| GB | 2136002 | 9/1954 |
| JP | 2002142723 | 5/2002 |
| WO | 2009101146 | 8/2009 |

OTHER PUBLICATIONS

Kong, Xiangzhen, Huiming Zhou, and Haifeng Qian. "Enzymatic hydrolysis of wheat gluten by proteases and properties of the resulting hydrolysates." Food Chemistry 102.3 (2007): 759-763.*
Wu Hui-Chun, et al. Free amino acids and peptides as related to antioxidant properties in protein hydrolysates of mackerel (*Scomber austriasicus*); XP 002502818; Food Research International; vol. 36, No. 9-10; accepted May 21, 2003, pp. 949-957.
Rebeca B. D. et al., "Production of Fish Protein Hydrolysates with Bacterial Proteases; Yield and Nutritional Value", Journal of Food Science —309, vol. 56, No. 2, 1991, XP-002502820.
Kristinsson, et al.; "Biochemical and Functional Properties of Atlantic Salmon (*Salmo salar*) Muscle Proteins Hydrolyzed with Various Alkaline Proteases"; Journal of Agricultural and Food Chemistry, vol. 48, No. 3, Mar. 2, 2000. XP-002502822.
Aspmo S. I., et al.; Enzymatic hydrolysis of Atlantic cod (*Gadus morhua* L.) viscera; Process of Biochemistry, Elsevier, NL.; vol. 40, No. 5, Apr. 1, 2005.
Guerard, et al., "Production of tuna waste hydrolysates by a commercial neutral protease preparation"; Journal of Molecular Catalysis B Enzymatic, Elsevier, Amsterdam, NL, No. 19-20; Dec. 2, 2002.
Ravallec-Ple, et al., The presence of bioactive peptides in hydrolysates prepared from processing waste of sardine (*Sardina pilchardus*); Journal of Science of Food and Agriculture, vol. 81, No. 11; Sep. 1, 2001; XP-002501882.
Picot et al., Antiproliferative activity of fish protein hydrolysates on human breast cancer cell lines, 2006, Process Biochemistry 41(5): 1217-1222.
Dumay et al., Improvement of lipid and phospholipid recoveries from sardine (*Sardina pilchardus*) viscera using industrial proteases, 2006, Process Biochemistry 41(11): 2327-2332.
Hoo et al., Optimization of enzymatic hydrolysis of Salmon (*Salmo salar*) skin by Alcalase, International Food Research Journal 18(4), 2011, pp. 1359-1365.
Setyorini et al., Purification and characterization of two novel halotolerant extracellular proteases from *Bacillus subtilis* strain FP-133, 2006, Bioscience, Biotechnology, and Biochemistry 70(2): 433-440.

* cited by examiner

*Primary Examiner* — Robert Yamasaki
(74) *Attorney, Agent, or Firm* — Thorpe North & Western LLP

(57) ABSTRACT

The present invention relates to a fish protein hydrolysate having a biological activity of interest, in particular an effect on the stimulation and maintenance of bone. The fish protein hydrolysate is characterized in that it is obtained by enzymatic hydrolysis of at least one protein source selected from the fish species *Micromesistius poutassou, Clupea harengus, Scomber scombrus, Sardina pilchardus, Trisopterus esmarki, Trachurus* spp, *Gadus morhua, Pollachius virens, Melanogrammus aeglefinus* and *Coryphaenoides rupestris*, and the species of fish belonging to the order Siluriformes, said enzymatic hydrolysis being carried out by means of an endopeptidase enzyme derived from *Bacillus subtilis*. The protein hydrolysate according to the invention makes it possible to maintain the bone mass or to stimulate bone growth through stimulation of osteoblast cell growth and inhibition of osteoclast cell growth.

7 Claims, 5 Drawing Sheets

Molecular weight, in Da

Molecular weight, in Da

Figure 1:
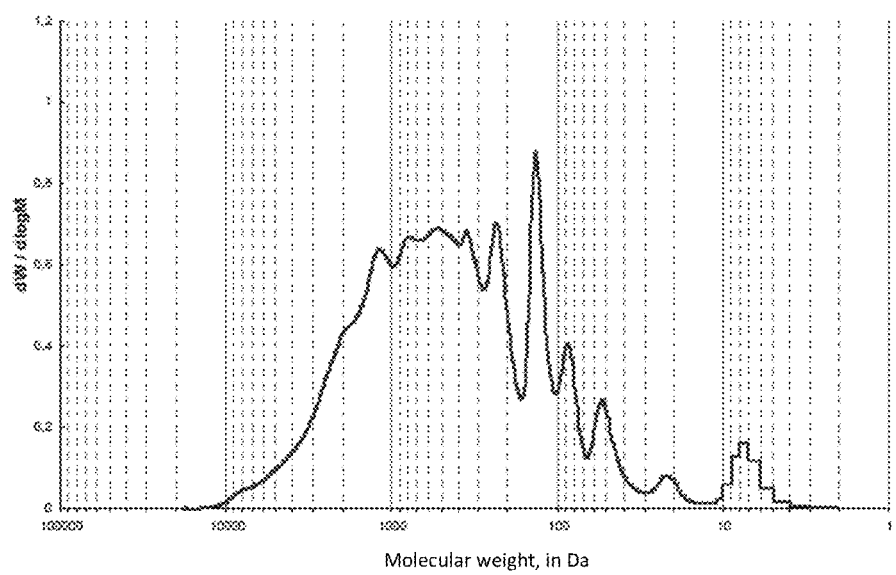
Figure 2:
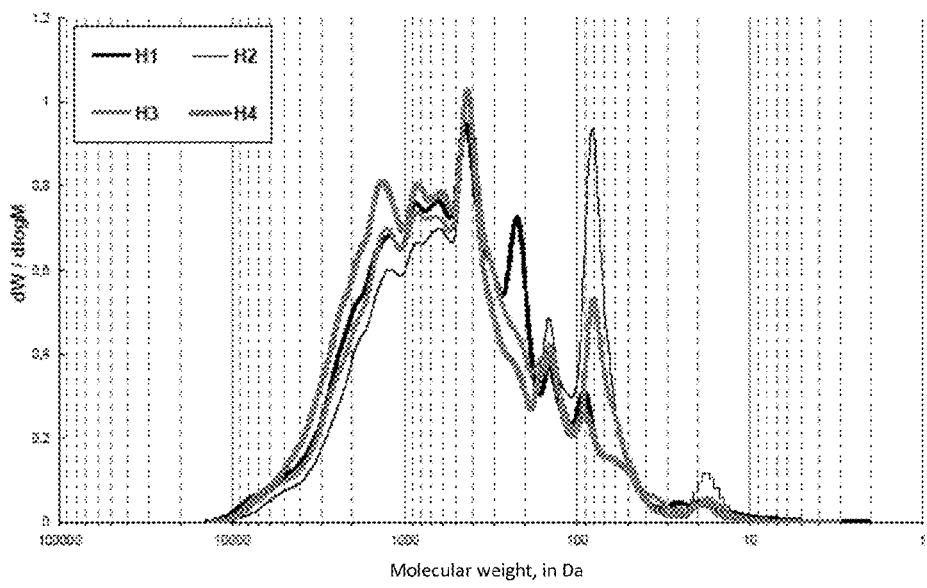
Figure 3:
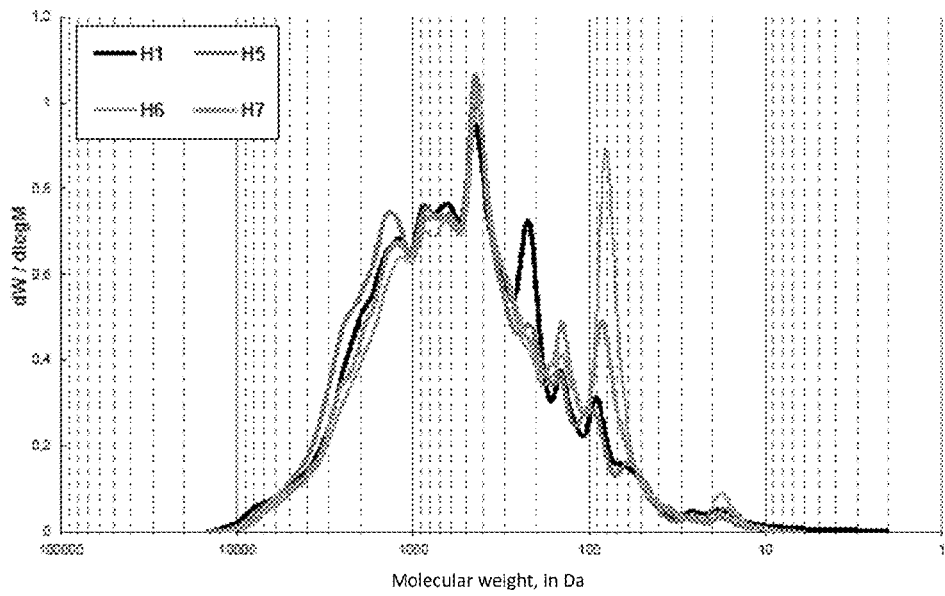
Figure 4:
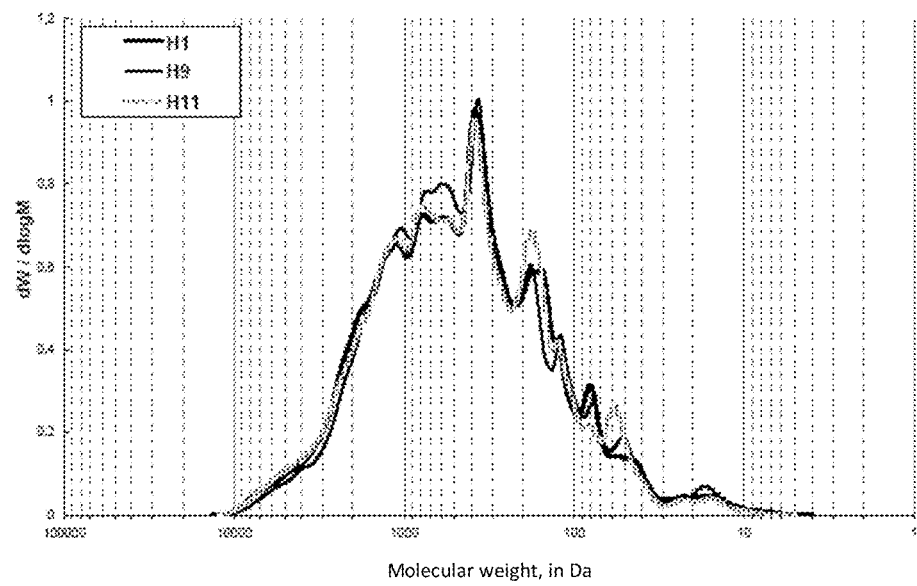

FISH PROTEIN HYDROLYSATE HAVING A BONE-STIMULATING AND MAINTAINING ACTIVITY, NUTRACEUTICAL AND PHARMACOLOGICAL COMPOSITIONS COMPRISING SUCH A HYDROLYSATE AND METHOD FOR OBTAINING SAME

This application is a continuation application of U.S. patent application Ser. No. 12/866,867, filed Nov. 3, 2010, which was a National Stage of International Application No. PCT/EP2009/051655, each of which are incorporated herein by reference.

The present invention concerns a fish protein hydrolysate having a biological activity of interest, in particular an effect on the stimulation and maintenance of the bone capital. The invention also concerns a method of obtaining such a fish protein hydrolysate, a food composition, a food supplement and a medication comprising such a fish protein hydrolysate.

Bone tissue is a specialised connective tissue that is composed in particular of osteoblast, osteocyte and osteoclast cells, collagen fibres and a mineralised matrix. Osteoblasts are responsible for synthesis of the bone tissue, in particular the synthesis of the bone matrix consisting of type-I collagen, proteoglycans and glycoproteins, whereas osteoclasts are responsible for bone resorption, that is to say the degradation of the bone tissue.

Bone tissue is constantly being renewed by virtue of a dynamic remodelling process occurring throughout the life. This remodelling is done by means of the combined action of osteoclasts and osteoblasts via the Basic Multicellular Unit (BMU). These units have a lifetime of approximately six months and renew approximately 10% of the skeleton per year.

A remodelling cycle begins with the activation of a new BMU on an inactive surface of the bone. The cells bordering the bone line will then disappear and be replaced by osteoclasts that hollow out a gap on the endosteal surface of the bone for approximately 2 weeks. This is the resorption phase. Once ended, the osteoclasts are destroyed by apoptosis and the pre-osteoblasts are differentiated. The mature osteoblasts can then synthesise the new bone matrix, in particular by continuously producing ossein, the organic component of the bone. Then this matrix is little by little mineralised and osteoblasts are trapped at the core of the matrix, thus becoming osteocytes (Hadjidakis et al, 2006).

Osteoporosis, or reduction in the bone capital, is a phenomenon observed in the whole of an ageing population. "Osteoporosis is a generalised disorder of the skeleton characterised by reduction in the bone density and an impairment of the micro-architecture of the bone tissue responsible for an increase in the fragility of the bone and consequently a risk of fracture" (WHO definition, 1992). This is an illness preferentially affecting women but, because of the extension of their life expectancy, men are no longer spared. This ailment is known to cause for example compression of the vertebrae, fractures of the wrist or fractures of the neck of the femur. The consequences of the fracture of the neck of femur are significant since they are accompanied by 20% mortality in the year following the fracture and in 50% of cases severe and incapacitating aftereffects.

At the menopause an oestrogen deficiency causes a reduction in bone formation, a deterioration in the architecture of the bone and a loss of bone mass thus giving rise to significant risk of fracture in the long term. Because of this oestrogen deficiency, bone renewal accelerates (increase in the number of BMUs), causing the appearance of greater porosity. Bone resorption greatly increases compared with formation, which for its part is not modified. This is principally due to an increase in the life of the osteoclasts.

In the current demographic context of a country such as France, where life expectancy is continually increasing, osteoporosis is today a major public health problem.

The importance of the role played by food in the acquisition of bone capital and its maintenance appears today to open the way to a very real prevention of this pathology. Thus a first approach is the modification of lifestyle, comprising dietary changes. The intake of dietary supplements alone or associated with changes in lifestyle is beneficial for leading to a maintenance of bone capital.

The applicants then discovered that fish protein or peptide hydrolysates obtained from the enzymatic hydrolysis of a source of proteins composed of certain fishes had properties of stimulating the growth of the bone mass. More particularly, the applicants discovered that such hydrolysates were capable of activating the growth of osteoblast cells and inhibiting the growth of osteoclast cells.

The invention thus concerns a fish protein hydrolysate that is characterised in that it is obtained by enzymatic hydrolysis of at least one source of proteins chosen from the species of pelagic fish *Micromesistius poutassou, Clupea harengus, Scomber scombrus, Sardina pilchardus, Trisopterus esmarki, Trachurus* spp, the demersal fish species *Gadus morhua, Pollachius virens, Melanogrammus aeglefinus, Coryphaenoides rupestris*, and fish species belonging to the order Siluriformes, the said enzymatic hydrolysis being carried out by means of an endopeptidase enzyme derived from *Bacillus subtilis* and in that it has the following physical and chemical characteristics:

the following molecular profile distribution: from 33% to 39% molecules with a molecular weight of less than 300 Da, from 34% to 37% molecules the molecular weight of which is between 300 and 1000 Da, from 21% to 24% molecules the molecular weight of which is between 10000 and 3000 Da, from 3% to 4% molecules the molecular weight of which is between 3000 and 5000 Da and 1% to 2% molecules the molecular weight of which is between 5000 and 10000 Da, a lipid content of less than 1% as a percentage of raw product, a glucid content of less than 4% as a percentage of raw product, a protein content of more than 80% as a percentage of raw product, a mineral matter content of between 5% and 10% as a percentage of raw product.

The protein hydrolysate according to the invention maintains the bone mass or stimulates bone growth. The protein hydrolysate according to the invention can be used in the prevention and treatment of ailments such as osteoporosis, for example post menopause, bone demineralisation, calcic malabsorption, malabsorption of vitamin D, and bone metabolism ailments. The protein hydrolysate according to the invention stimulates the growth of osteoblast cells and inhibits the growth of osteoclast cells, as demonstrated by the following examples.

According to one feature of the invention, the fish protein hydrolysate has the following amino acid composition: Glutamic acid 16.9%, Aspartic acid 11.7%, Lysine 10%, Leucine 8.2%, Arginine 6.3%, Alanine 6.8%, Valine 4.8%, Isoleucine 4.4%, Glycine 5%, Threonine 4.5%, Serine 4.4%, Tyrosine 3.2%, Phenylalanine 3.9%, Methionine 2.6%, Proline 3.4%, Histidine 2%, Cystine 1%, Tryptophan 0.8%, as a percentage by weight with respect to the total weight of amino acids.

According to a preferred embodiment of the invention, the said fish protein source comprises the pulp of the fillet of the said fish or fishes.

The present invention also concerns a method of obtaining a protein hydrolysate from a fish protein source, the said hydrolysate having properties of maintaining or stimulating the growth of the bone mass. The method according to the invention is characterised in that it comprises:

- the grinding of at least one protein source chosen from the pelagic fish species *Micromesistius poutassou, Clupea harengus, Scomber scombrus, Sardina pilchardus, Trisopterus esmarki, Tracharus* spp, the demersal fish species *Gadus morhua, Pollachius virens, Melanogrammus aeglefinus, Coryphaenoides rupestris*, and fish species belonging to the order Siluriformes, in the presence of water, so as to recover the fish pulp,
- the enzymatic hydrolysis of the said protein source at a temperature of between 50° and 75° C., for 1 to 5 hours, after the addition of an endopeptidase enzyme derived from *Bacillus subtilis*, so as to obtain a reaction mixture.
- stoppage of the said enzymatic hydrolysis by deactivation of the said enzyme after raising the temperature of the said reaction mixture to a level not below 70° C., for 8 to 20 minutes,
- the separation of the protein hydrolysate obtained from the rest of the reaction mixture.

The enzymatic hydrolysis of the pulp of the aforementioned fish according to the method according to the invention makes it possible to obtain a fish protein hydrolysate having properties of regulating the growth of the bone mass. The enzymatic hydrolysis is performed by an enzyme carefully selected to make it possible to obtain a protein hydrolysate having the aforementioned properties sought. The method, through the nature of the enzyme, the hydrolysis temperature and the absence of solvents respects the organoleptic and nutritional qualities of the hydrolysate obtained. This hydrolysate can then be incorporated in food compositions or pharmaceutical preparations.

According to one feature of the invention, an endopeptidase enzyme derived from *Bacillus subtilis* is the product Corolase N sold by the company AB Enzyme (Feldbergstrasse 78, D-64293, Darmstadt, Germany).

Preferably, the said grinding of the protein source is carried out in the presence of water in a protein source/water ratio of 1.

According to one embodiment of the invention, the said enzymatic hydrolysis is performed in accordance with an enzyme/protein source ratio between 0.1 and 1%. Preferentially, the enzyme/protein source ratio is 0.75%.

Advantageously, the said enzymatic hydrolysis is carried out at a temperature of 55° C.

The separation of the protein hydrolysate obtained from the rest of the reaction mixture is generally performed by centrifugation at a speed of between 4000 and 7000 rev/min and elimination of the residue obtained.

Advantageously, the separation of the protein hydrolysate obtained is performed by filtration of the said reaction mixture prior to the said centrifugation. Filtration of the reaction medium eliminates the solid matter.

According to one embodiment of the invention, the said method also comprises the concentration and atomisation or freeze drying of the said hydrolysate obtained.

According to another embodiment of the invention, the said enzymatic hydrolysis is stopped by increasing the temperature of the said reaction mixture up to 85° C. and maintaining this temperature for 15 minutes.

According to one embodiment of the invention, the said grinding of the said protein source is carried out using the fillet of the said fish or fishes.

The present invention also concerns a fish protein hydrolysate obtained by a method as described previously. Such a hydrolysate is as defined previously.

The present invention also concerns a composition, a food supplement and a food composition comprising a fish protein hydrolysate as described previously.

The present invention also concerns a medication comprising a fish protein hydrolysate as described previously, as well as the use of such a fish protein hydrolysate for manufacturing a medication for treating or preventing osteoporosis, for example post menopause, bone demineralisation, calcic malabsorption, malabsorption of vitamin D, and bone metabolism ailments.

The fish protein hydrolysate according to the invention is also used in stimulating the growth of osteoblasts and inhibiting the growth of osteoclasts.

The nutraceutical or pharmaceutical formulations incorporating a fish protein hydrolysate according to the invention can comprise ingredients normally used in this type of formulation such as binders, flavourings, preservatives or colourings and, in the case of food supplements or medications, may be in the form of tablets, granules or capsules. Formulations according to the invention can also be in the form of food products such as drinks, or in the form of suspensions or syrups.

The features of the invention mentioned above, as well as others, will emerge more clearly from a reading of the following description of an example embodiment, the said example being intended to be illustrative and non-limitative.

Figure 5:
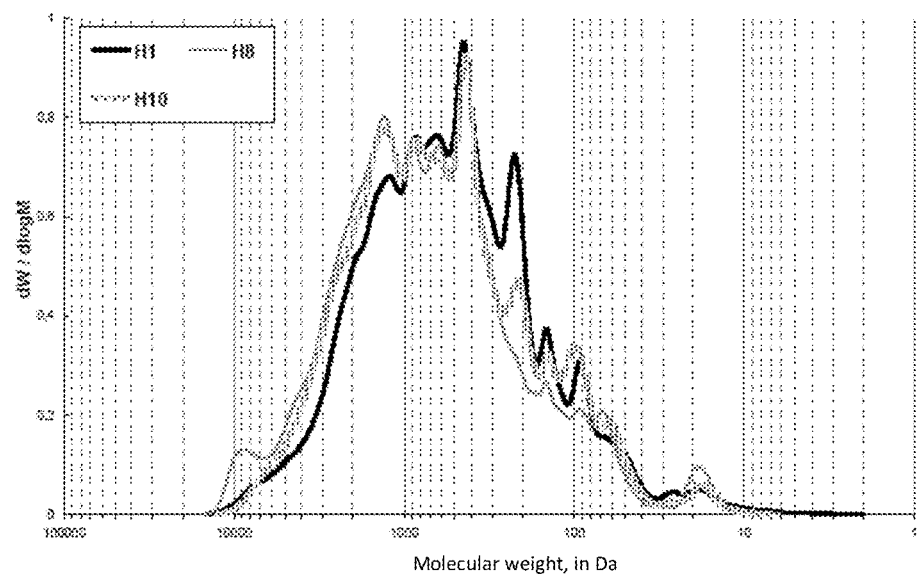
Figure 6:
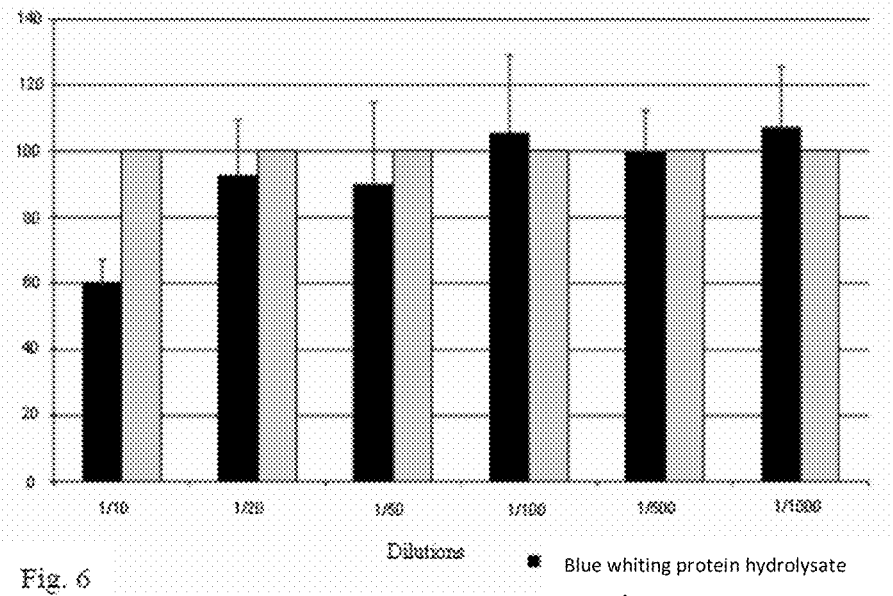
Figure 7:
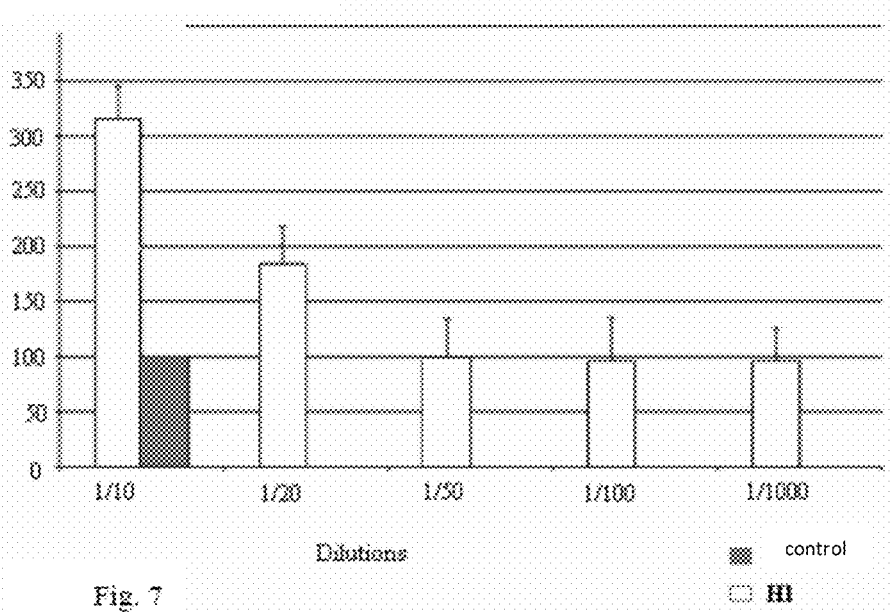
Figure 8:
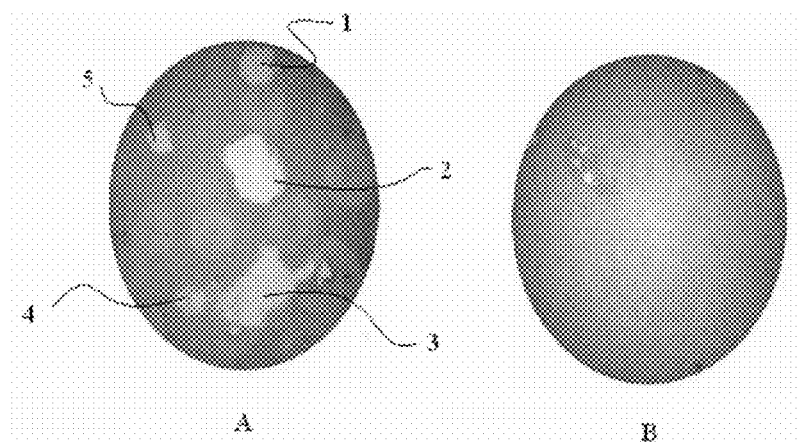
Figure 9:
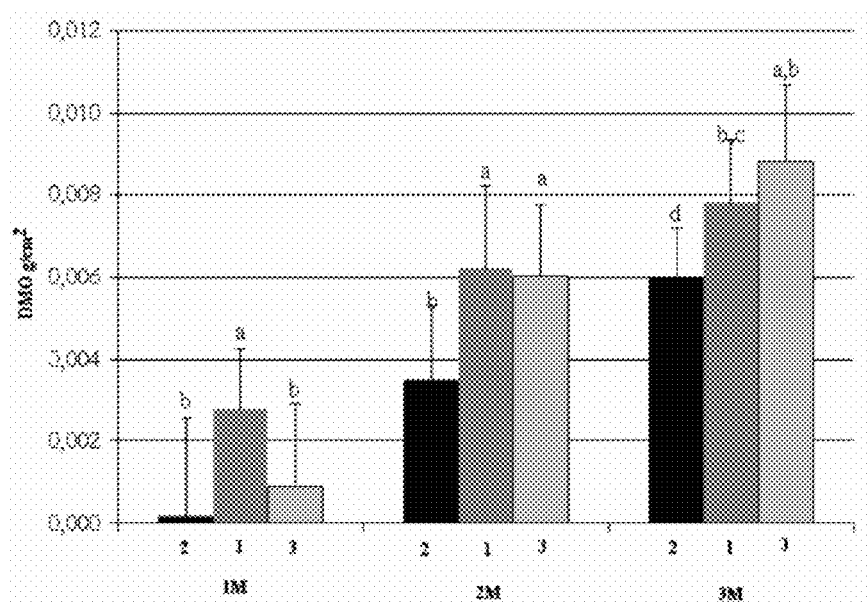

FIG. 1 illustrates the distribution of the molecular weights of the protein fragments of a blue whiting protein hydrolysate according to the invention, and FIGS. 2 to 5 illustrate the distribution of the molecular weights of the protein fragments of protein hydrolysates of other species of fish according to the invention, FIGS. 6 and 7 illustrate the effect on the growth of bone cells of a blue whiting protein hydrolysate according to the invention, FIG. 8 illustrates the inhibition of the growth of osteoclasts by a blue whiting hydrolysate according to the invention, FIG. 9 illustrates an effect of a blue whiting protein hydrolysate according to the invention on the bone mineral density in mice.

EXAMPLE 1

Protein Hydrolysate Obtained from Blue Whiting

The blue whiting (*Micromesistius poutassou*) is fished in the North Atlantic off Newfoundland. The fish are cut into fillets, which are then ground so as to obtain pulp therefrom. This fish pulp constitutes a source of protein for the production of the hydrolysate. The pulp is stored at −20° C. until use.

Three kilos of previously thawed blue whiting pulp are mixed with water in a ratio by weight of 1. The temperature is raised to 55° C. and an endopeptidase enzyme derived from *Bacillus subtilis*, sold under the name Corolase N by the company AB Enzyme (Feldbergstrasse 78, D-64293, Darmstadt, Germany) is then added to the reaction medium in an enzyme/protein source ratio of 0.75%.

The hydrolysis reaction is carried out for 2 hours and then the enzyme is deactivated by raising the temperature of the reaction medium to 85° C. This temperature is maintained for 15 minutes.

The blue whiting protein hydrolysate obtained, hereinafter referred to as H1, is then filtered on a sieve (mesh 2 mm/2 mm) so as to eliminate the solid matter and then recovered in a receptacle. The fraction recovered in the receptacle is then centrifuged for 30 minutes±5 minutes, at a speed of between 4000 and 7000 rpm. After elimination of the residue, the supernatant is recovered, freeze dried and stored in a cool dry place, away from light. The supernatant can also be atomised.

Physical and Chemical Analyses of the H1 Protein Hydrolysate Obtained from Blue Whiting A determination of the molecular weights of the peptides making up the H1 protein hydrolysate obtained is carried out by steric exclusion chromatography (SEC-HPLC).

The protein hydrolysate, in the form of powder after freeze drying, is suspended in ultra-pure water at 20 mg/ml and then filtered on a 0.45 μm membrane and analysed by filtration over gel with a Superdex Peptide HR 10/30 column, sold by the company Pharmacia. The matrix of the column is composed of a crosslinked porous gel (diameter 13-15 μm) of agarose and dextran with a total volume of 24 ml. Its fractionation domain is between 100 and 7000 Da. The column is mounted on an HPLC line (sold by the company Dionex) equipped with a pump (Dionex P680 module). The measurement is carried out by a multiwavelength ultraviolet detector (Dionex UVD 170 U module). The HMB protein hydrolysate is eluted by a mobile phase containing acetonitrile, water and TFA. The elution lasts for approximately 1 hour at a rate of 0.5 ml/min.

The distribution of molecular weights is calculated from the parameters of a calibration line obtained after passage through the column of the following markers with known molecular weights: Cytochrome C (12,400 Da), aprotinin (6511 Da), gastrin I (2126 Da), the substance P fragment 1-7 (1348 Da), glycine (75 Da) and leupeptin (463 Da). The data are collected by means of Chromeleon software (Dionex). The percentages of the molecular weights are calculated by means of software (GPC Cirrus from Polymer Laboratories). The acquisition wavelength is 214 nm. The distribution of the molecular weights as a function of dW/log M is given by the software and is shown in FIG. 1. The percentage of the area under the curve corresponds to the percentage of molecules. The distribution of the molecular weights by class of size is given in table 1:

TABLE 1

| Classes | H1 | H2 | H3 | H4 | H5 | H6 | H7 | H8 | H10 | H9 | H11 |
|---|---|---|---|---|---|---|---|---|---|---|---|
| <0.3 | 33-39 | 38 | 33 | 33 | 33 | 35 | 33 | 33 | 33 | 36 | 34 |
| 0.3-1 | 34-37 | 37 | 37 | 37 | 37 | 37 | 37 | 37 | 36 | 37 | 37 |
| 1-3 | 21-24 | 21 | 24 | 24 | 24 | 22 | 24 | 24 | 24 | 22 | 23 |
| 3-5 | 3-4 | 3 | 4 | 4 | 4 | 4 | 4 | 4 | 4 | 3 | 4 |
| 5->10 | 1-2 | 1 | 2 | 2 | 2 | 2 | 2 | 2 | 2 | 2 | 2 |

The amino acid composition of the blue whiting protein hydrolysate H1 is given in table 2 and is obtained according to the indications in European Directive 98/64/CE and NF EN ISO 13904-October 2005.

TABLE 2

| Amino acid | Percentage of amino acid |
|---|---|
| Glutamic acid | 16.9 |
| Lysine | 10 |
| Aspartic acid | 11.7 |
| Leucine | 8.2 |
| Arginine | 6.3 |
| Alanine | 6.8 |

TABLE 2-continued

| Amino acid | Percentage of amino acid |
|---|---|
| Valine | 4.8 |
| Isoleucine | 4.4 |
| Cystine | 1 |
| Glycine | 5 |
| Threonine | 4.5 |
| Serine | 4.4 |
| Tyrosine | 3.2 |
| Phenylalanine | 3.9 |
| Methionine | 2.6 |
| Proline | 3.4 |
| Histidine | 2 |
| Tryptophan | 0.8 |

The protein content is above 80%, by percentage of raw product (NF V18-120-March 1997—corrected KJELDAHL).

The lipid content is less than 1%, as a percentage of raw product (according to European Directive 98/64/CE).

The energy value of the protein hydrolysate H1 is approximately 350 Kcal/100 g.

The glucid content is less than 4% (deduced from the protein and glucid contents and the energy value).

EXAMPLE 2

Protein Hydrolysate Obtained from Other Species of Fish According to the Invention Hydrolysates of proteins of mackerel (H2) (*Scomber scombrus*), horse mackerel (H3) (*Trachurus* spp.) grenadier (H4) (*Coryphaenoides rupestris*) (FIG. 2); bib (H5) (*Trisopterus esmarki*), sardine (H6) (*Sardina pilchardus*) herring (H7) (*Clupea harengus*), panga (H8) and (*Suliforme*) pollock (H10) (*Pollachius virens*) FIG. 5; cod (H9) (*Gadus morhau*) and haddock (H11) (*Melanogrammus aeglefinus*) (FIG. 4) were prepared according to the method of example 1. The distribution of the molecular weights of the peptides making up each hydrolysate was analysed according to the same method as that used in example 1.

The distribution of the molecular weights as a function of dW/log M is given in FIGS. 2 to 5, and a distribution of the molecular weights by class of size is given in the following table 1. The percentage of the area under the curve corresponds to the percentage of peptide molecules.

All the hydrolysates show identical molecular weight distribution profiles.

EXAMPLE 4

Biological Activities of the H1 Protein Hydrolysate

In Vitro Study:

The H1 protein hydrolysate was tested vis-á-vis its ability to promote the stimulation of the growth of osteoblast cells and to cause inhibition of the growth of osteoclast cells on in vitro cell cultures.

The H1 protein hydrolysate in the form of powder after freeze drying was suspended in ultra-pure water at the rate of 20 mg/ml, and then filtered on a 0.22 micron membrane in order to sterilise it. Various dilutions were then produced: 1/10 (i.e. the highest peptide concentration, that is to say 2 mg/ml), 1/20 (1 mg/ml), 1/50 (0.4 mg/ml), 1/100 (0.2 mg/ml), 1/500 (0.04 mg/ml) and 1/1000 (0.02 mg/ml).

Cell Cultures:

Mixed bone cell cultures, that is to say consisting of osteoblasts and osteoclasts, issuing from mice in the BalB/c strain, were produced as follows.

The mice were killed by decapitation and the bones of the back legs were taken under aseptic conditions and then placed in a sterile tube containing liquid Minimum Essential Medium-α (MEM-α) culture (1×), supplemented with Earle salts, glutamax I (Invitrogen Corporation, 1600 Faraday Ave., Carlsbad, Calif. 92008), ribonucleosides and deoxyribonucleosides.

The leg bones were scraped with a scalpel and then reduced into small pieces in order to extract the bone marrow. The cells and all the debris were collected in a tube, which was subjected to vigorous stirring for approximately 2 minutes in order to detach the cells from the bone debris. The suspension was then filtered on a filter with a porosity of 70 μm. The cells were recovered by centrifugation (5 minutes at 800 g), the supernatant was eliminated and the cell residues recovered in a complete culture medium (MEM-α supplemented with penicillin/streptomycin, 10% foetal calf serum and $10^{-8}$ of $1\alpha,25\text{-}(OH)_2D_3$ or $1\alpha,25$-dihydroxyvitamin $D_3$).

The cells thus obtained from 4 or 5 tibias were then seeded in a 75 cm² flask. The culture flasks were incubated at 37° C. in a moist atmosphere containing 5% $CO_2$. The time necessary for the adhesion of the cells to the surface of the flask was approximately 5 hours. After this period necessary for the attachment of the osteoblast and osteoclast precursors, the medium was replaced at the rate of 15 ml for a surface of 75 cm². The medium was changed twice a week. After 6 days of culturing, the medium was aspirated. The cells were detached from the flask by means of a scraper and then put in suspension at a density of $1.2 \times 10^4$ cells/ml. These culture conditions enable the osteoblasts and osteoclasts to grow.

The next day, the medium was changed and the H1 protein hydrolysate was added to the culture medium at the various dilutions mentioned previously (1/10, 1/20, 1/50, 1/500 and 1/1000).

A solution of bovine serum albumin (BSA) (20 mg/ml) was prepared as a reference (BSA reference) and added to the cells under the same dilution conditions as the other protein solutions.

A reference culture (negative reference) is used and corresponds to a culture of bone cells in which neither the H1 protein hydrolysate nor the BSA were added.

Cell Growth of a Mixed Cell Culture: Qualification of DNA

Quantification of the DNA makes it possible to evaluate the effect of the various proteins, H1 or BSA, on the cell growth of the mixed cell cultures.

This is a fluorometric analysis carried out using the FluoroReporter Blue Fluorometric dsDNA Quantification Kit (F-2962) (Molecular Probes; Invitrogen Corp).

The cells incubated in the presence of various dilutions of the H1 protein hydrolysate, the cells incubated in the presence of the BSA reference solution, and the reference culture cells, are lysed by freezing in order to release the DNA. The Hoechst 33258 reagent used in the kit is specific to regions rich in A-T sequences of the newly synthesised double-strand DNA, to which it binds. The bonding is detected by fluorescence.

FIG. 6 present the effect of the H1 protein hydrolysate at different concentrations on the growth of the bone cells from mice in the BalB/c strain. The results are expressed as a percentage with respect to the reference culture.

The H1 protein hydrolysate significantly inhibits the growth of bone cells (inhibition of 40% at 1/10). This is because, the presence of a reference protein solution, the BSA, the growth of the bone cells is 100% whereas in the presence of a solution of an H1 protein hydrolysate diluted at 1/10, the growth of bone cells is 60%.

In order to determine whether the cells the growth of which is inhibited are osteoclasts or osteoblasts, a supplementary analysis was carried out. This analysis is based on analysis of the alkaline phosphatase that is secreted specifically by osteoblasts. Thus, by measuring the activity of the alkaline phosphatase and expressing the results obtained as a function of the quantification of the DNA previously described, it is possible to determine whether the H1 protein hydrolysate is favourable to the development of osteoblasts and inhibits osteoclasts.

Stimulation of Osteoblast Growth: The Apportioning of Alkaline Phosphatase 4-methylumbelliferyl phosphate (4-MUP) (Sigma-Aldrich Corporation, 3050 Spruce St, St Louis, Mo. 63103) is an alkaline phosphatase substrate.

The dephosphorylation of the substrate by the alkaline phosphatase is measured by fluorescence.

The substrate was added to the cell culture media to which the various dilutions of the H1 protein hydrolysate were previously added as well as to the reference cell culture medium (reference culture).

FIG. 7 presents the activity of alkaline phosphatase (AP) expressed as percentage, according to the various dilutions of the H1 protein hydrolysate and also in the absence of protein hydrolysate (reference culture).

Knowing that a value of 100% of alkaline phosphatase activities is obtained for the reference culture, we find that the 1/10 and 1/20 dilutions of H1 protein hydrolysate are capable of stimulating the differentiation of the osteoblasts. The 1/10 dilution multiplies by three the activity of the alkaline phosphatase and consequently increases the differentiation of the osteoblasts by three compared with the reference culture. Taking account of this, it appears that the inhibition of the bone cell growth observed previously concerned the osteoclasts rather than the osteoblasts.

Inhibition of the Growth of Osteoclasts: Digestion of a Bone Substrate

The primary cultures of mixed mouse cells were cultivated on a synthetic bone substrate. The mature osteoclasts present in the mixed cell cultures are capable of digesting a bone substrate.

The H1 protein hydrolysate, diluted to $1/10^{th}$, was added to the cell culture medium.

A control corresponding to a cell culture on the bone substrate in the absence of H1 protein hydrolysate was implemented.

FIG. 8 presents two photographs that were produced with a microscope in the presence of the H1 protein hydrolysate (FIG. 8A) or in the absence of the H1 protein hydrolysate (control, FIG. 8B).

The photographs show digestion zones (1, 2, 3, 4, 5) visible on the control bone substrate (FIG. 8A) whereas the bone substrate visible in FIG. 8B is not digested. The H1 protein hydrolysate therefore reduced the activity of the osteoclasts. These results, combined with those of the quantification of the DNA presented above, make it possible to conclude that the H1 protein hydrolysate inhibits the growth of osteoclasts.

EXAMPLE 5

Biological Activities of the H1 Protein Hydrolysate

In Vivo Study:

During this study, an ovariectomised mouse model was used in order to cause an oestrogen deficiency and to mimic a menopause phenomenon. A regime containing 14% by weight H1 fish protein hydrolysates was compared with a reference standard regime containing 14% by weight total milk proteins.

The changes in the total bone mineral density were monitored over time.

Thirty-six 10-week old C3H/Hen mice, supplied by the Harlan breeding centre, were placed in cages within a room thermostatically controlled at 22° C. in a reverse day-night cycle (night from 6 am to 6 μm). The animals were habituated to their environment and to their food in the form of powder for 2 weeks. Each animal received water and food ad libitum (5 grams per day and per mouse) during the 3 months of study.

At twelve weeks, the mice were subjected to ovariectomy or surgery without removal of the ovaries. Following the operation, the animals were distributed into 3 groups of 12 according to the regimes that they were to receive:

Group 1 (positive reference). The mice are operated on without suffering removal of the ovaries and receive the control regime, that is to say 40% total milk proteins (casein and lactoserum included).

Group 2 (negative reference). The mice undergo ovariectomy and receive the control regime.

Group 3. The mice were operated on in order to undergo removal of the ovaries and receive a regime containing 14% H1 (same composition as the control regime but the milk proteins are replaced by the fish protein hydrolysates obtained in example 1).

All the regimes provided contain 14% proteins and have similar energy compositions as indicated by table 3 below.

TABLE 3

| | Constituents in g/kg of regime groups 1 and 2 | Constituents in g/kg of regime group 3 |
|---|---|---|
| Total milk proteins | 140.0 | 0.0 |
| H1 (powder) | 0.0 | 140.0 |
| Total Kcal/kg of regime | 3671.4 | 3582.8 |

Monitoring of Change in Bone Mineral Density (BMD)

The bone density is the reflection of the quality of the bone and its strength. This measurement, serving as a reference for diagnosis of osteoporosis, is made by biphoton absorptiometry using X-rays (DEXA: Dual Energy X-ray Absorptiometry). The apparatus, the PIXImus densitometer (LUNAR CORPORATION, Madison, Wis.), emits X-rays that pass through the body of the mouse and sensors detect the attenuation of the intensity of the X-ray beam through the calcified bone regions. It also determines the surface area and the mass of calcified bone tissues and "soft" tissues passed through. Thus the lean mass, the fat mass and the total BMD (the quantity of bone in grams on the bone surface of the body in $cm^2$) can be evaluated. To make the measurements, the mice are anaesthetised (by a xylazine/ketamine mixture) and placed in a plastic dish on the apparatus platform. This produces an image, which is retranscribed on a screen. The images obtained can then be reprocessed by focussing on a precise part of the body of the mouse: such as the femurs and the vertebral column. This is because, these bones being rich in spongy bone, they are more easily affected by osteoporosis.

The BMD was evaluated just before the ovariectomy, and every month following the operation. All these operations were performed within the IFR 02 of the UFR Medicale Paris 7.

Results

FIG. 9 shows the total gain in bone mineral density (BMD) over time and according to the groups (1, 2 and 3). The values are given in the form of mean±standard deviation. The groups with different letters are statistically different ($p<0.05$).

At time 0, before ovariectomy, the groups had BMDs that were comparable with one another. In order to have a better idea of the effect of the regimes, the total gains in BMD were studied. In all cases, the BMD increases over time. After one month of regime (1M), the operation effect is at a maximum since group 1 has a BMD significantly superior to all the other groups, that is to say these mice continue to acquire bone whereas the bone growth is stopped in the animals that suffer an oestrogen deficiency. After two months of regime (2M), the BMD of group 3 catches up that of group 1 and is significantly different from that of group 2. Therefore, for these two groups, a regime effect is clearly observed as from two months.

Finally, at 3 months of regime (3M), groups 1 and 2 are still statistically different. The animals in group 3 have a significantly greater gain in BMD than those of group 2 and are not statistically different from those of group 1.

The removal of the ovaries causes a drop in the bone mineral density. The differences between group 2 (ovariectomised) and group 1 persist over time, proving the effect of the oestrogen deficiency on the mineralisation of the bone and the validity of the model. Finally, group 3 very significantly increases the bone mineralisation, exceeding the gain in BMD of the reference groups 1 and 2. There is therefore indeed an effect of the H1 fish hydrolysate protein fraction on the total bone mineralisation. These results confirm those obtained previously during the in vitro study, which would demonstrate the ability of the hydrolysates according to the invention to increase the differentiation of the osteoblasts while reducing that of the osteoclasts (example 4).

The invention claimed is:

1. A method to increase bone mineral density in a human in need thereof comprising, administrating to the human a pharmaceutical or nutritional composition comprising a *Bacillus subtilis* endopeptidase enzyme treated *Micromesistius poutassou* fish protein hydrolysate.

2. The method of claim 1, wherein the fish protein hydrolysate is obtained by a process, comprising:
   grinding of *Micromesistius poutassou* as protein source,
   enzymatic hydrolyzing said protein source at a temperature of between 50° and 75° C., for 1 to 5 hours, after the addition of an endopeptidase enzyme derived from *Bacillus subtilis*, in a ratio of enzyme to protein source of between 0.01 and 2%, so as to obtain a reaction mixture,
   stopping said enzymatic hydrolysis by inactivation of the said enzymes after raising the temperature of the said reaction mixture to a level not below 70° C., for 8 to 20 minutes, and
   separating the protein hydrolysate obtained from the rest of the reaction mixture.

3. The method according to claim 2, wherein a source of fish protein comprises pulp obtained from a fillet of the said fish.

4. The method according to claim 3, wherein an enzyme to protein source ratio is 0.75%, the said hydrolysis temperature is 55° C.

5. The method according to claim 4, wherein the fish protein hydrolysate has the following amino acid composition: Glutamic acid 16.9%, Aspartic acid 11.7%, Lysine 10%, Leucine 8.2%, Arginine 6.3%, Alanine 6.8%, Valine 4.8%, Isoleucine 4.4%, Glycine 5%, Threonine 4.5%, Serine 4.4%, Tyrosine 3.2%, Phenylalanine 3.9%, Methionine 2.6%, Proline 3.4%, Histidine 2%, Cystine 1%, Tryptophan 0.8%, as a percentage by weight with respect to the total weight of amino acids.

6. The method of according to claim 4, wherein the fish protein hydrolysate is in the form of a food product, a food supplement, or a neutraceutical composition.

7. The method according to claim 1, wherein the fish protein hydrolysate has the following molecular profile distribution:

from 33% to 39% molecules with a molecular weight of less than 300 Da, from 34% to 37% molecules the molecular weight of which is between 300 and 1000 Da, from 21% to 24% molecules the molecular weight of which is between 1000 and 3000 Da, from 3% to 4% molecules the molecular weight of which is between 3000 and 5000 Da and 1% to 2% molecules the molecular weight of which is between 5000 and 10000 Da, a lipid content of less than 1% as a percentage of raw product, a glucid content of less than 4% as a percentage of raw product, a protein content of more than 80% as a percentage of raw product, and a mineral matter content of between 5% and 10% as a percentage of raw product.

\* \* \* \* \*